(12) United States Patent
Koele et al.

(10) Patent No.: US 7,862,550 B2
(45) Date of Patent: *Jan. 4, 2011

(54) MECHANICAL FASTENING SYSTEM FOR AN ABSORBENT ARTICLE

(75) Inventors: Mathew L. Koele, Chilton, WI (US); Robert L. Popp, Neenah, WI (US); William M. Lynch, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 63 days.

This patent is subject to a terminal disclaimer.

(21) Appl. No.: 12/359,863

(22) Filed: Jan. 26, 2009

(65) Prior Publication Data

US 2009/0131895 A1     May 21, 2009

Related U.S. Application Data

(63) Continuation of application No. 11/196,169, filed on Aug. 3, 2005, now Pat. No. 7,497,851, which is a continuation of application No. 10/038,675, filed on Dec. 31, 2001, now Pat. No. 6,969,377.

(51) Int. Cl.
*A61F 13/15*     (2006.01)

(52) U.S. Cl. ..................... 604/391; 604/387

(58) Field of Classification Search ................ 604/367, 604/385.01, 391; 428/198, 93, 96; 24/451–452

See application file for complete search history.

(56) References Cited

U.S. PATENT DOCUMENTS

| | | | |
|---|---|---|---|
| 2,957,512 A | 10/1960 | Wade et al. | |
| 3,276,944 A | 10/1966 | Levy | |
| 3,319,307 A | 5/1967 | Marforio | |
| 3,338,992 A | 8/1967 | Kinney | |
| 3,341,394 A | 9/1967 | Kinney | |
| 3,502,538 A | 3/1970 | Peteresen | |
| 3,542,615 A | 11/1970 | Dobo et al. | |
| 3,577,607 A | 5/1971 | Ikoma et al. | |
| 3,692,618 A | 9/1972 | Dorschner et al. | |

(Continued)

FOREIGN PATENT DOCUMENTS

EP     0 217 032 A1     4/1987

(Continued)

OTHER PUBLICATIONS

International Search Report for PCT/US 02/37896 dated Jun. 11, 2003.

(Continued)

*Primary Examiner*—Michele Kidwell
(74) *Attorney, Agent, or Firm*—Armstrong Teasdale, LLP

(57) ABSTRACT

A mechanical fastening system for an article having a stretchable loop fastener component mountable on the article and including an elastomeric substrate and a high bond point non-woven loop material secured to the elastomeric substrate. The bond points on the non-woven loop material are defined by discrete compression points and the non-woven loop material is substantially free from discrete compression points other than at the bond points. A hook fastener component is mountable on the article and adapted for releasable engagement with the loop fastener component. The stretchable loop fastener component is stretchable relative to the hook fastener component when the fastener components are engaged.

12 Claims, 5 Drawing Sheets

U.S. PATENT DOCUMENTS

| | | |
|---|---|---|
| 3,694,867 A | 10/1972 | Stumpf |
| 3,800,796 A | 4/1974 | Jacob |
| 3,802,817 A | 4/1974 | Matsuki et al. |
| 3,943,981 A | 3/1976 | DeBrabander |
| 4,035,559 A | 7/1977 | Fujii et al. |
| 4,051,853 A | 10/1977 | Egan, Jr. |
| 4,205,679 A | 6/1980 | Repke et al. |
| 4,209,563 A | 6/1980 | Sisson |
| 4,340,563 A | 7/1982 | Appel et al. |
| 4,606,964 A | 8/1986 | Wideman |
| 4,610,680 A | 9/1986 | LaFleur |
| 4,615,695 A | 10/1986 | Cooper |
| 4,640,726 A | 2/1987 | Sallee et al. |
| 4,657,802 A | 4/1987 | Morman |
| 4,663,220 A | 5/1987 | Wisneski et al. |
| 4,699,622 A | 10/1987 | Toussant et al. |
| 4,704,116 A | 11/1987 | Enloe |
| 4,705,710 A | 11/1987 | Matsuda |
| 4,714,096 A | 12/1987 | Guay |
| 4,739,635 A | 4/1988 | Conley et al. |
| 4,741,949 A | 5/1988 | Morman et al. |
| 4,761,318 A | 8/1988 | Ott et al. |
| 4,803,117 A | 2/1989 | Daponte |
| 4,826,499 A | 5/1989 | Ahr |
| 4,834,741 A | 5/1989 | Sabee |
| 4,834,742 A | 5/1989 | Wilson et al. |
| 4,834,820 A | 5/1989 | Kondo et al. |
| 4,847,134 A | 7/1989 | Fahrenkrug et al. |
| 4,850,990 A | 7/1989 | Huntoon et al. |
| 4,894,060 A | 1/1990 | Nestegard |
| 4,896,378 A | 1/1990 | Camapana |
| 4,936,840 A | 6/1990 | Proxmire |
| 4,940,464 A | 7/1990 | Van Gompel et al. |
| 4,963,140 A | 10/1990 | Robertson et al. |
| 4,965,122 A | 10/1990 | Morman |
| 4,981,747 A | 1/1991 | Morman |
| 5,019,073 A | 5/1991 | Roessler et al. |
| 5,032,120 A | 7/1991 | Freeland et al. |
| 5,032,122 A | 7/1991 | Noel et al. |
| 5,046,272 A | 9/1991 | Vogt et al. |
| 5,087,253 A | 2/1992 | Cooper |
| 5,104,116 A | 4/1992 | Pohjola |
| 5,114,781 A | 5/1992 | Morman |
| 5,116,662 A | 5/1992 | Morman |
| 5,125,246 A | 6/1992 | Shytles |
| 5,143,679 A | 9/1992 | Weber et al. |
| 5,176,670 A | 1/1993 | Roessler et al. |
| 5,176,671 A | 1/1993 | Roessler et al. |
| 5,224,405 A | 7/1993 | Pohjola |
| 5,226,992 A | 7/1993 | Morman |
| 5,236,430 A | 8/1993 | Bridges |
| 5,256,231 A | 10/1993 | Gorman et al. |
| 5,318,555 A | 6/1994 | Siebers et al. |
| 5,326,612 A | 7/1994 | Goulait |
| 5,336,545 A | 8/1994 | Morman |
| 5,370,634 A | 12/1994 | Ando et al. |
| 5,374,262 A | 12/1994 | Keuhn, Jr. et al. |
| 5,380,313 A | 1/1995 | Goulati et al. |
| 5,383,872 A | 1/1995 | Roessler et al. |
| 5,386,595 A | 2/1995 | Kuen et al. |
| 5,407,439 A | 4/1995 | Goulait |
| 5,453,318 A | 9/1995 | Giacobbe |
| 5,476,702 A | 12/1995 | Datta et al. |
| 5,547,531 A | 8/1996 | Allen et al. |
| 5,586,371 A | 12/1996 | Thomas |
| 5,595,567 A | 1/1997 | King et al. |
| 5,614,281 A | 3/1997 | Jackson et al. |
| 5,615,460 A | 4/1997 | Weirich et al. |
| 5,616,394 A | 4/1997 | Gorman et al. |
| 5,622,578 A | 4/1997 | Thomas |
| 5,624,427 A | 4/1997 | Bergman et al. |
| 5,628,741 A | 5/1997 | Buell et al. |
| 5,647,864 A | 7/1997 | Allen et al. |
| 5,664,302 A | 9/1997 | Thomas |
| 5,669,900 A | 9/1997 | Bullwinkel et al. |
| 5,669,901 A | 9/1997 | LaFortune et al. |
| 5,681,302 A | 10/1997 | Melbye et al. |
| 5,693,401 A | 12/1997 | Sommers et al. |
| 5,699,593 A | 12/1997 | Jackson |
| 5,707,707 A | 1/1998 | Burnes et al. |
| 5,735,840 A | 4/1998 | Kline et al. |
| 5,763,041 A | 6/1998 | Leak et al. |
| 5,766,389 A | 6/1998 | Brandon et al. |
| 5,785,699 A | 7/1998 | Schmitz |
| 5,786,062 A | 7/1998 | Callahan, Jr. et al. |
| 5,795,350 A | 8/1998 | Schmitz |
| 5,830,206 A | 11/1998 | Larsson |
| 5,830,298 A | 11/1998 | Jackson |
| 5,853,881 A | 12/1998 | Estey et al. |
| 5,855,574 A | 1/1999 | Kling et al. |
| 5,858,515 A | 1/1999 | Stokes et al. |
| 5,867,925 A | 2/1999 | Fattori |
| 5,883,028 A | 3/1999 | Morman et al. |
| 5,888,607 A | 3/1999 | Seth et al. |
| 5,891,547 A | 4/1999 | Lawless |
| 5,897,545 A | 4/1999 | Kline et al. |
| 5,897,547 A | 4/1999 | Scmitz |
| 5,901,419 A | 5/1999 | Widlund et al. |
| 5,910,136 A | 6/1999 | Hetzler et al. |
| 5,914,084 A | 6/1999 | Benson et al. |
| 5,916,207 A | 6/1999 | Toyoda et al. |
| 5,938,648 A | 8/1999 | LaVon et al. |
| 5,953,797 A | 9/1999 | Provost et al. |
| 5,964,742 A | 10/1999 | McCormack et al. |
| 5,997,981 A | 12/1999 | McCormack et al. |
| 6,018,852 A | 2/2000 | Coslovi et al. |
| 6,027,485 A | 2/2000 | Matsushita et al. |
| 6,036,805 A | 3/2000 | McNichols |
| 6,086,571 A | 7/2000 | Guevara et al. |
| 6,102,901 A | 8/2000 | Lord et al. |
| 6,113,717 A | 9/2000 | Vogt et al. |
| 6,136,405 A | 10/2000 | Young et al. |
| 6,142,986 A | 11/2000 | Lord et al. |
| 6,146,738 A | 11/2000 | Tsuji et al. |
| 6,150,002 A | 11/2000 | Varona |
| 6,192,556 B1 | 2/2001 | Kikko et al. |
| 6,197,404 B1 | 3/2001 | Varona |
| 6,210,389 B1 | 4/2001 | Long et al. |
| 6,287,287 B1 | 9/2001 | Elsberg |
| 6,301,755 B1 | 10/2001 | Gaber |
| 6,328,725 B2 | 12/2001 | Fernfors |
| 6,329,016 B1 | 12/2001 | Shepard et al. |
| 6,332,250 B1 | 12/2001 | Igaue et al. |
| 6,417,121 B1 | 7/2002 | Newkirk et al. |
| 6,417,122 B1 | 7/2002 | Newkirk et al. |
| 6,420,285 B1 | 7/2002 | Newkirk et al. |
| 6,461,344 B1 | 10/2002 | Widlund et al. |
| 6,475,600 B1 | 11/2002 | Morman et al. |
| 6,647,549 B2 | 11/2003 | McDevitt et al. |
| 2002/0173767 A1 | 11/2002 | Popp et al. |
| 2003/0045856 A1 | 3/2003 | Couture et al. |

FOREIGN PATENT DOCUMENTS

| | | |
|---|---|---|
| EP | 0 463 276 A1 | 1/1992 |
| EP | 0 812 584 A2 | 12/1997 |
| EP | 0 638 304 B1 | 3/1999 |
| EP | 0 800 379 B1 | 12/1999 |
| EP | 0 782 424 B1 | 7/2000 |
| EP | 1159945 A1 | 12/2001 |
| FR | 1.375.254 | 10/1964 |
| GB | 2 387 180 A1 | 10/2003 |
| WO | 92/01401 A1 | 2/1992 |
| WO | 96/03101 A1 | 2/1996 |

| | | | |
|---|---|---|---|
| WO | 97/19808 A1 | 6/1997 |
| WO | 97/25893 A1 | 7/1997 |
| WO | 98/29503 A1 | 7/1998 |
| WO | 98/29504 A1 | 7/1998 |
| WO | 99/14045 A1 | 3/1999 |
| WO | 99/65441 A1 | 12/1999 |
| WO | 00/35395 A2 | 6/2000 |
| WO | 00/35395 A3 | 6/2000 |
| WO | 00/35398 A1 | 6/2000 |
| WO | 00/37009 A2 | 6/2000 |
| WO | 00/37009 A3 | 6/2000 |
| WO | 01/87206 A1 | 11/2000 |
| WO | 01/87208 A1 | 11/2001 |
| WO | 01/87209 A1 | 11/2001 |
| WO | 01/87753 A2 | 11/2001 |
| WO | 01/96113 A1 | 12/2001 |

OTHER PUBLICATIONS

International Search Report for PCT/US 02/40780 dated Apr. 22, 2003.

MECHANICAL FASTENING SYSTEM FOR AN ABSORBENT ARTICLE

CROSS-REFERENCE TO RELATED APPLICATION

This application is a continuation of U.S. patent application Ser. No. 11/196,169, filed Aug. 3, 2005, which is a continuation of U.S. patent application Ser. No. 10/038,675, filed Dec. 31, 2001. Both of these applications are hereby incorporated in their entirety.

BACKGROUND OF THE INVENTION

The present invention pertains to absorbent articles, such as training pants, diapers, incontinence garments and the like, and more particularly, to a mechanical fastening system for such absorbent articles.

Such absorbent articles generally comprise a liquid-impermeable barrier sheet, a liquid permeable body side liner and an absorbent medium between them. They generally include some type of attaching system for fitting the article to the wearer. In many such applications, the fastening system is preferably refastenable so that the article can be temporarily removed and then refastened to the wearer.

One common form of mechanical attachment systems is the so called hook-and-loop system which comes in various forms and has both advantages and disadvantages in its application to such absorbent articles. For example, particularly with diapers, the fasteners are secured to the garment in the front and back, generally in such a manner that the back portion of the fasteners on each side are pulled over the front portion to secure the garment to the wearer. In typical such products the loop material is relatively unstretchable and either forms a portion of the garment itself or is attached to the surface of the garment. The hook material is generally attached to an extensible substrate so that it can be positioned on the loop material for adjustment to the size and shape of the wearer of the garment.

A disadvantage of this type of hook-and-loop system is the tendency of the hooks to separate from the loop material when the wearer is active, such as when stooping or bending as is common with a child in diapers. This disengagement failure can result in the garment coming loose from the wearer (with possible leakage resulting) thus requiring it to be refastened, if possible. This produces an undesirable inconvenience and disadvantage of such a mechanical fastening system for such applications. In an attempt to overcome this disadvantage many systems have increased the force to disengage through various enhancements in strengthening both the hook-and-loop material.

SUMMARY OF THE INVENTION

In one aspect, a mechanical fastening system for an article generally comprises a stretchable loop fastener component mountable on the article and comprising an elastomeric substrate and a high bond point non-woven loop material secured to the elastomeric substrate. The bond points on the non-woven loop material are defined by discrete compression points. The non-woven loop material is substantially free from discrete compression points other than at the bond points. A hook fastener component is mountable on the article and adapted for releasable engagement with the loop fastener component. The stretchable loop fastener component is stretchable relative to the hook fastener component when the fastener components are engaged.

BRIEF DESCRIPTION OF THE DRAWINGS

The above-mentioned and other features of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the drawings.

DEFINITIONS

Figure 1:
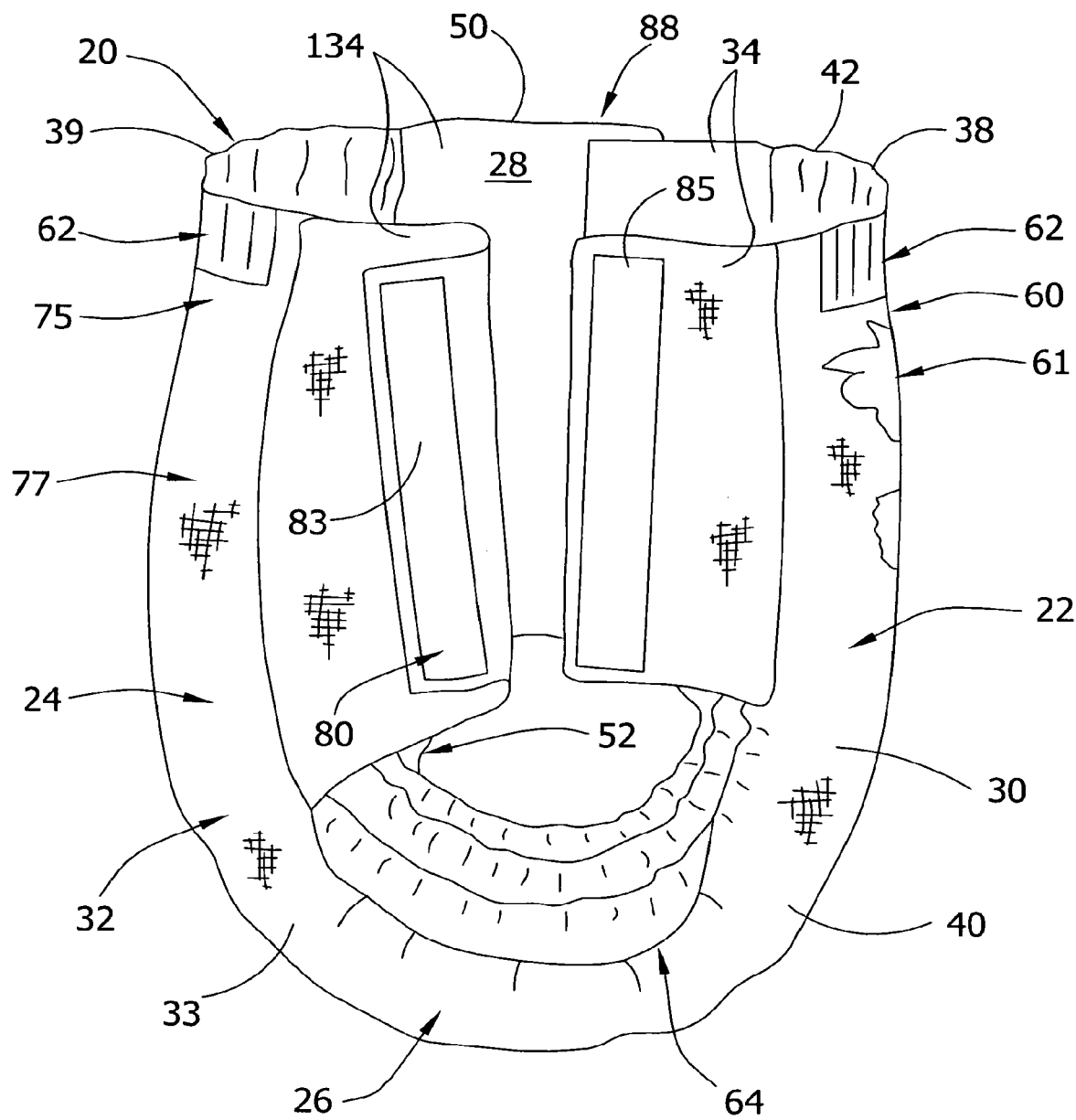
FIG. 1 illustrates a side view of a training pant according to the present invention, where the fastening system is shown engaged on one side of the training pant and disengaged on the other side of the training pant.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 901 are designated "wettable" or hydrophilic, while fibers having contact angles greater than 901 are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
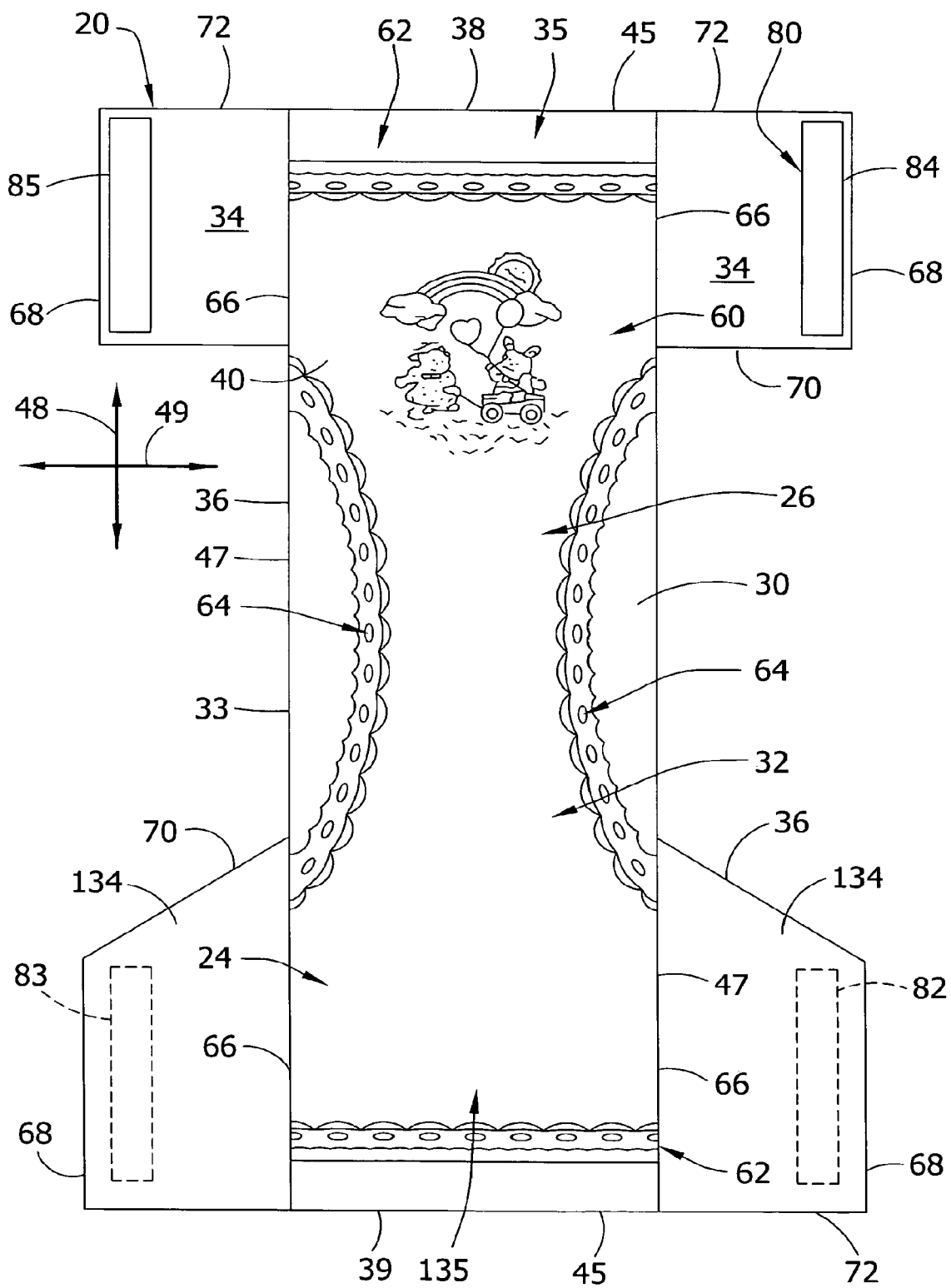
FIG. 2 illustrates a plan view of the training pant shown in FIG. 1 in an unfastened, stretched and laid flat condition, and showing the surface of the training pant that faces away from the wearer.
Figure 3:
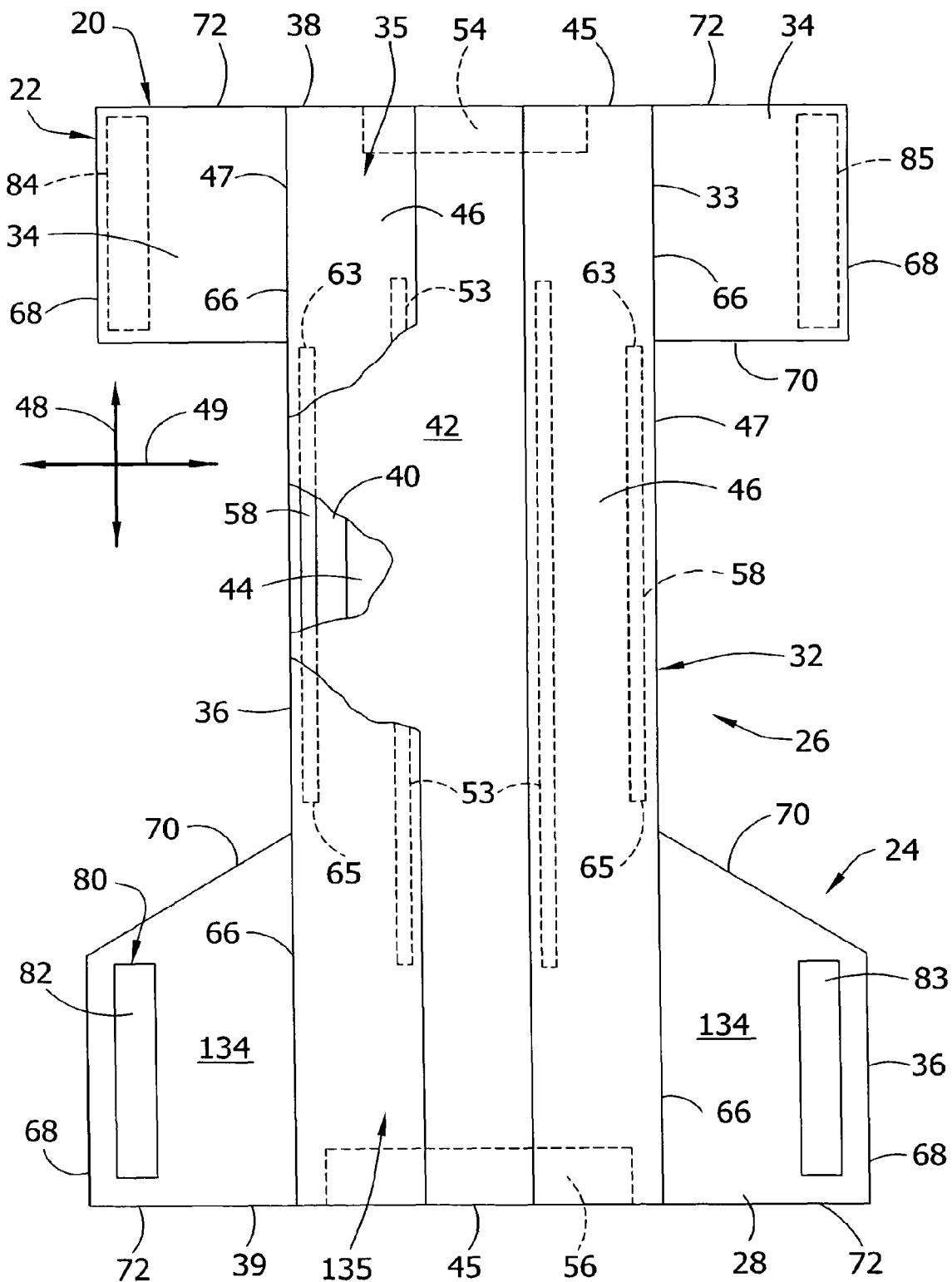
FIG. 3 illustrates a plan view similar to FIG. 2, but showing the surface of the training pant that faces the wearer when the training pant is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a nonsoftened condition when cooled to room temperature.

These terms may be defined with additional language in the remaining portions of the specification.

DETAILED DESCRIPTION OF THE PREFERRED EMBODIMENTS

FIG. 1 representatively illustrates one embodiment of training pant 20 in a partially fastened condition. The training pant 20 comprises an absorbent body 32 and a fastening system 80. The absorbent body 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent body 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent body 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a bodyside liner 42 (FIG. 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent body 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent body 32 includes the transversely opposed front side panels 34 and a front center panel 35 (FIGS. 2 and 3) positioned between and interconnecting the side panels. The back waist region 24 of the absorbent body 32 includes the transversely opposed back side panels 134 and a back center panel 135 (FIGS. 2 and 3) positioned between and interconnecting the side panels. The waist edges 38 and 39 of the absorbent body 32 are configured to encircle the waist of the wearer when worn and provide the waist opening 50 which defines a waist perimeter dimension. Portions of the transversely opposed side edges 36 in the crotch region 26 generally define the leg openings 52. The waist regions 22 and 24 jointly define a waistband 75 (FIGS. 1, 4 and 7) that peripherally surrounds the waist opening 50 of the pant 20. The waist regions 22 and 24 also jointly define a hip section 77 (FIGS. 1, 4 and 7) that encircles the pant 20 and is disposed between the waistband 75 and the leg openings 52.

The absorbent body 32 is configured to contain and/or absorb any body exudates discharged from the wearer. For example, the absorbent body 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent body 32, and can extend longitudinally along the entire length of the absorbent body or may only extend partially along the length of the absorbent body. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges, such that the waist elastic members are disposed in the waistband 75 in the fully assembled pant. The leg elastic members 58 are desirably operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

In particular embodiments, the waist elastic members 54 and 56 can be formed of retractive materials. For example, the waist elastic members 54 and 56 can be formed of an elastomeric material that is adapted to retract upon activation by a source of heat such as disclosed in U.S. Pat. No. 4,640,726.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spun-bonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent body 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent body 32. These transversely opposed front side panels 34 and transversely opposed back side panels 134 can be permanently bonded along attachment lines 66 to the composite structure 33 of the absorbent body 32 in the respective front and back waist regions 22 and 24. More particularly, as shown best in FIGS. 2 and 3, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the bodyside liner, and/or another component of the absorbent body.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent body 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent body 32, and the waist end edges 72 of the back side panels 134 form part of the back waist edge 39 of the absorbent body.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown). The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material comprises a stretch-thermal laminate, a neck-bonded laminate, a reversibly necked laminate, or a stretch-bonded laminate material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically prestrained materials; and/or stretchable but inelastic materials.

In particular embodiments, one or more of the side panels 34 and 134 can be formed of retractive materials. For example, the side panels 34 and 134 can be formed of an elastomeric material that is adapted to retract upon activation by a source of heat, such as disclosed in U.S. Pat. No. 4,640,726.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners including high bond point nonwoven facings. In another particular embodiment, the first fastening components 82 and 83 each comprise loop type fasteners including high bond point nonwoven facings and the second fastening components 84 and 85 each comprise complementary hook type fasteners. Although the illustrated embodiments show the back waist region 24 overlapping the front waist region 22, which is convenient, the training pant 20 can also be configured so that the front waist region overlaps the back waist region.

Figure 4:
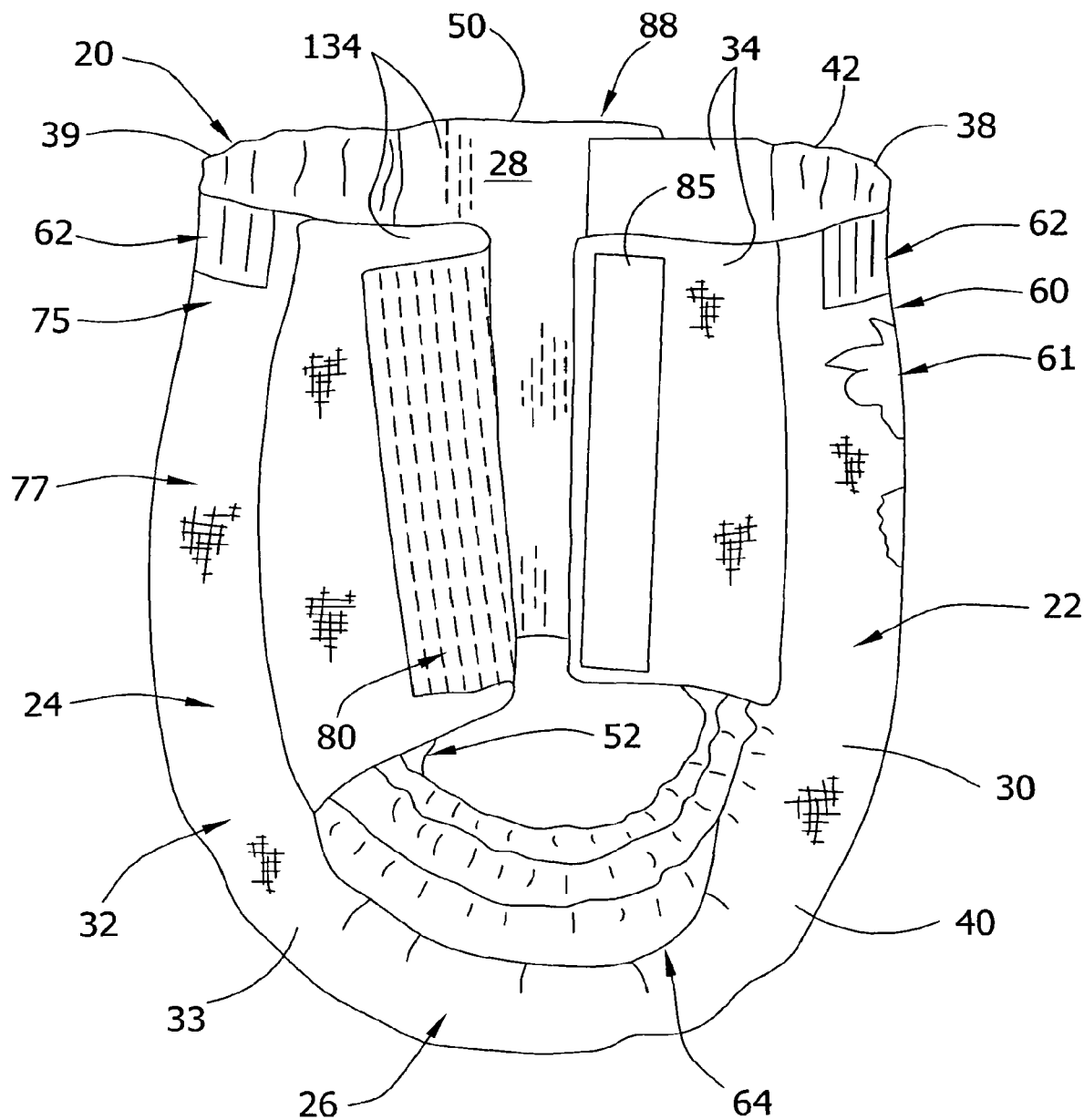
FIG. 4 illustrates an alternative embodiment of the present invention in a side view similar to FIG. 1.
Figure 5:
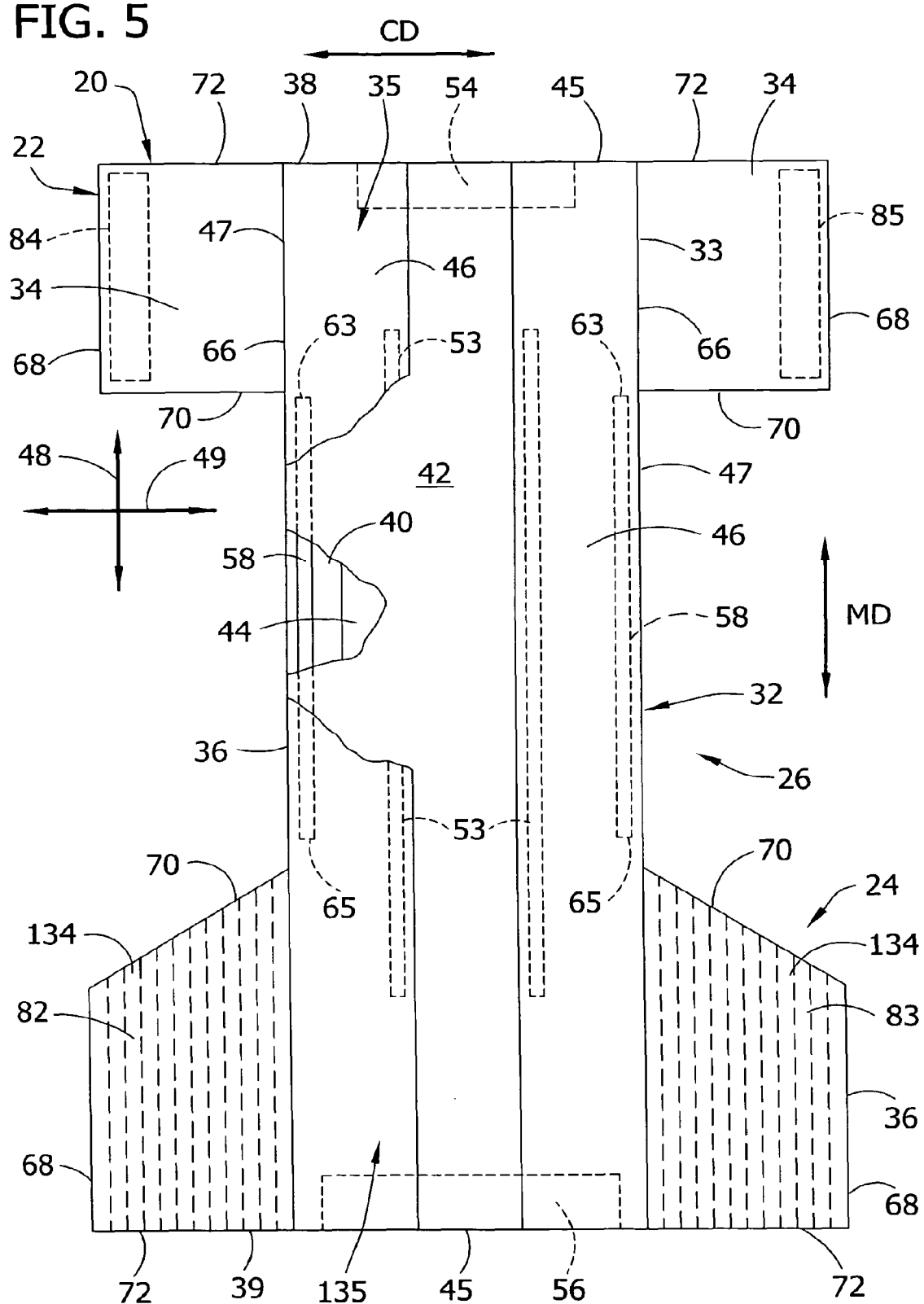
FIG. 5 is a plan view of the embodiment of FIG. 4 in a similar position as FIG. 3.

A wide variety of other arrangements of fastening components can be employed. For example, the training pant 20 can include only a single fastening component disposed in one waist region for refastenably connecting to at least one fastening component disposed in the opposite waist region (not shown). In a further alternative embodiment illustrated in FIGS. 4 and 5, the fastening components can comprise integral portions of the waist regions. For instance, the front and/or back side panels 34 and 134 can function as fastening components in that they can comprise a material that is releasably engageable with fastening components disposed in the opposite waist region. As illustrated in FIGS. 4 and 5, the side panels 134 can be made completely of stretchable loop material although, alternatively, the side panels could be made of loop material only at there outer ends and the remainder of the side panels can be made of some other, preferably stretchable, material and joined along abutting edges thereof.

Hook type fasteners typically comprise a fabric or material having a base or backing structure and a plurality of hook members extending upwardly from at least one surface of the backing structure. The hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82-85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In accordance with the present invention, the loop type fasteners comprise high bond point nonwoven facings. In particular embodiments, the loop type fasteners can be made of stretchable loop materials including high bond point facings, and the stretchable loop materials can be disposed on the product so that the material is free to stretch during use of the product. With particular reference to FIG. 3, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 2, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks. The loop fastening components can be integral with the side panels or adhered to the side panels 34 and 134 by any means known to those skilled in the art such as adhesive bonds, sonic bonds or thermal bonds. The loop fastening components can be extensible and bonded to components of the body 32 in a manner that retains extension and retraction characteristics of the loop fastening components.

The fastening components are desirably rectangular, although they may alternatively be square, round, oval, curved or otherwise non-rectangularly shaped. In particular embodiments, each of the fastening components 82-85 defines a length dimension aligned generally parallel with the longitudinal axis 48 of the training pant 20 and a width dimension aligned generally parallel with the transverse axis 49 of the training pant. For a child of about 9 to about 15 kilograms (20-30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82-85 are releasably engaged, the side edges 36 of the absorbent body 32 in the crotch region 26 define the leg openings 52, the waist edges 38 and 39 of the absorbent body, including the waist end edges 72 of the side panels, define the waist opening 50, and the waist regions 22 and 24 jointly define a waistband 75 and hip section 77. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82-85 form refastenable seams 88 (FIG. 1) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal centerlines of the fasteners, measured with the side panels 34 and 134 in an unstretched condition.

The inventors have determined that high bond point nonwoven facings, and in particular high bond point nonwoven facings with bond point densities greater than 225 pins per square inch, are especially suited for use as loop fastening components. The high bond point nonwoven facings can also have a total bond area greater than 10 percent. The terms "total bond area" and "bond area" are used interchangeably and refer to the surface area of interfiber bonds of a nonwoven web, expressed as a percent. An example of such facings include the wire weave bond pattern material with 304 pins per square inch constructed as disclosed in U.S. Pat. No. 5,964,742, which is incorporated herein by reference. In particular embodiments, the high bond point nonwoven facings can have a total bond area from about 15 to about 24 percent, although bond areas as high as 40 percent can be acceptable in certain fastener constructions. In other respects, a wide range of hook-and-loop materials may be suitable for use in the present invention.

In particular embodiments, the nonwoven facing material comprises a spunbond nonwoven web of substantially continuous fibers. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,276,944 to Levy, U.S. Pat. No. 3,502,538 to Peterson, and U.S. Pat. No. 3,542,615 To Dobo et al., all of which are incorporated herein by reference. Fiber deniers for such materials typically range from 1 to 10 deniers, but 1.5 to 4 deniers are preferred. The smaller fibers are easier for the hooks to catch, however, the smaller fibers tend to break more easily. Nonwoven fabrics are generally bonded in some manner as they produced in order to give them sufficient structural integrity to withstand the rigors of further processing into a finished product. Thermal bonding is the method preferred in this invention. Thermal bonding of a nonwoven may be accomplished by passing the nonwoven fabric between the rolls of a calendaring machine. At least one of the rollers of the calendar is heated and at least one of the rollers, not necessarily the same one as the heated one, has a pattern which is imprinted upon the nonwoven fabric as it passes between the rollers. As the fabric passes between the rollers it is subjected to pressure as well as heat. The combination of heat and pressure applied in a particular pattern results in the creation of fused bond areas in the nonwoven fabric where the bonds on the fabric correspond to the pattern of bond points on the calendar roll. It is believed that the combination of bond densities greater than 225 pins per square inch with bond areas greater than 10 percent, such as 10 to 40 percent, and particularly 10 to 30 percent, provide optimal number of bonded loops or fibers for engagement while also allowing optimal unbonded space for hooks to engage theses loops in a hook and loop fastening system.

High bond point nonwoven facings work exceptionally well as a loop material. The bond points made by the bond pins can be of different sizes and shapes which will change the bond area for a given number of bond points. Therefore there is a range of bond area to bond points that work particularly well in this invention. In particular embodiments, the high bond point nonwoven facing has greater than 10 percent bond area, in combination with greater than 225 points per square inch, particularly greater than 250 points per square inch, more particularly greater than 275 points per square inch, and still more particularly greater than 300 points per square inch. In other embodiments, the high bond point nonwoven facing has greater than 20 percent bond area, in combination with greater than 225 points per square inch, particularly greater than 250 points per square inch, more particularly greater than 275 points per square inch, and still more particularly greater than 300 points per square inch. In further embodiments, the high bond point nonwoven facing has greater than 25 percent bond area, in combination with greater than 225 points per square inch, particularly greater than 250 points per square inch, more particularly greater than 275 points per square inch, and still more particularly greater than 300 points per square inch. In still further embodiments, the high bond point nonwoven facing has greater than 30 percent bond area, in combination with greater than 225 points per square inch, particularly greater than 250 points per square inch, more particularly greater than 275 points per square inch, and still more particularly greater than 300 points per square inch.

The nonwoven facing having the relatively high density of bond points can be laminated to another substrate to form a loop material laminate. The nonwoven facing can be gathered or ungathered when bonded to the other substrate, and similarly the other substrate can be gathered or ungathered when bonded to the nonwoven facing. The other substrate to which the nonwoven facing is bonded can comprise an inelastic material such as another nonwoven or a film. In particular embodiments, for example, the high bond point nonwoven facing can be bonded to an inelastic layer of a disposable absorbent article, such as a layer forming an outer cover of the article. The nonwoven facing can itself comprise an elastomeric material. In alternative embodiments, the high bond point nonwoven facing can be bonded to an elastic substrate to form an elastomeric laminate. In such embodiments, the elastic substrate can be made from any material which may be manufactured in sheet or web form. Generally, any suitable elastomeric fiber forming resins or blends containing the same may be utilized. The elastic substrate can comprise elastomeric fibers, threads, filaments, and/or strands, nonwoven webs of elastomeric fibers, threads, filaments, and/or strands, elastomeric films, or the like. Useful elastic substrates may have basis weights ranging from about 5 gsm (grams per square meter) to about 300 gsm, for example, from about 5 gsm to about 150 gsm.

For example, an elastic substrate may be made from block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The elastic substrate may be formed from, for example, (polystyrene/poly(ethylene-butylene)/polystyrene) block copolymers available from the Shell Chemical Company under the trademark KRATON G. One such block copolymer may be, for example, KRATON™ G-1657.

Other exemplary elastomeric materials which may be used to form an elastic substrate include polyurethane elastomeric materials such as, for example, those available under the trademark ESTANE from B. F. Goodrich & Co., polyamide elastomeric materials such as, for example, those available under the trademark PEBAX from the Rilsan Company, and polyester elastomeric materials such as, for example, those available under the trade designation Hytrel from E. I. DuPont De Nemours & Company.

Formation of elastic substrates from polyester elastic materials is disclosed in, for example, U.S. Pat. No. 4,741,949 to Morman et al., hereby incorporated by reference. An elastic substrate may also be formed from elastic copolymers of ethylene and at least one vinyl monomer such as, for example, vinyl acetates, unsaturated aliphatic monocarboxylic acids, and esters of such monocarboxylic acids. The elastic copolymers and formation of elastic substrates from those elastic copolymers are disclosed in, for example, U.S. Pat. No. 4,803,117.

Processing aids may be added to the elastomeric polymer. For example, a polyolefin may be blended with the elastomeric polymer (e.g., the A-B-A elastomeric block copolymer) to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothene NA 601 (also referred to herein as PE NA 601 or polyethylene NA 601). Two or more of the polyolefins may be utilized. Extrudable blends of elastomeric polymers and polyolefins are disclosed in, for example, U.S. Pat. No. 4,663,220 to Wisneski et al., hereby incorporated by reference. The elastic substrate may also be a pressure sensitive elastomer adhesive sheet or web.

The elastic substrate may also be a multilayer material in that it may include two or more individual coherent webs and/or films. Additionally, the elastic substrate may be a multilayer material in which one or more of the layers contain a mixture of elastic and nonelastic fibers or particulates. An example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such an elastic composite web would be one made by a technique such as disclosed in previously referenced U.S. Pat. No. 4,741,949. That patent discloses an elastic nonwoven material which includes a mixture of meltblown thermoplastic fibers and other materials. The fibers and other materials are combined in the gas stream in which the meltblown fibers are borne so that an intimate entangled commingling of meltblown fibers and other materials, e.g., wood pulp, staple fibers or particulates such as, for example, hydrocolloid (hydrogel) particulates commonly referred to as super-absorbents occurs prior to collection of the fibers upon a collecting device to form a coherent web of randomly dispersed fibers.

The high bond point nonwoven facing can be joined to another substrate, whether elastic or inelastic, by any suitable means such as, for example, adhesives, hydraulic entangling, thermal bonding or ultrasonic welding. Thermal and/or ultrasonic joining techniques are believed to soften at least portions of at least one of the materials, which is usually the elastic substrate when employed because the elastomeric materials tend to have a lower softening point than the components of the high bond point material. Joining may be produced by applying heat and/or pressure to the high bond point material and the other substrate by heating these portions to at least the softening temperature of the material with the lowest softening temperature to form a reasonably strong and permanent bond between the re-solidified softened portions of one material and the other material.

In embodiments where a stretch bonded laminate is formed, the high bond point material should be joined to the tensioned elastic substrate at least at three locations which are arranged so that upon release of the tensioning force on the elastic substrate, puckers or gathers form in the high bond point material between at least two of the locations. The three or more locations should be arranged in a nonlinear configuration to form, for example, a triangular or polygonal pattern of locations where the high bond point material is joined to the elastic substrate. By way of illustration, the high bond point nonwoven can be formed into an elastomeric laminate in the manner described in U.S. Pat. No. 5,116,662, which is incorporated herein by reference.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. Hence, the processing conditions necessary to achieve satisfactory bonding can be readily determined for a given combination of materials.

To the extent that the high bond point material exhibits some resistance to being gathered, the elastic substrate will be unable to fully recover to its unstretched dimension once it is joined to the high bond point material. This requires that the distance that the elastic substrate is capable of stretching when it is joined to the high bond point material be greater than the desired stretch of the elastic composite material in the direction that the high bond point material cannot be easily extended (e.g., the machine direction). For example, if it is desired to prepare an elastic composite material that can be elongated about 100 percent in the machine direction (i.e., stretched to a length that is about 200 percent of its initial relaxed length), a 100 cm length of elastic web may be stretched in the machine direction to a length of, for example, 220 cm (120 percent elongation) and bonded at least at three locations (arranged in spaced-apart non-linear configuration) to a 220 cm length of high bond point material. The bonded composite elastic material is then allowed to relax and even if the elastic substrate is capable of recovering to its original 100 cm length, the high bond point material bonded thereto will inhibit full recovery and the composite may relax to a length of say, 110 cm. Puckers or gathers will form in the high bond point material between at least two of the bond points. The resulting 110 cm length of composite material is stretchable in the machine direction to its 220 cm length to provide a composite material that can be elongated about 100 percent in the machine direction (i.e., stretched to a length that is about 200 percent of its initial relaxed length). The initial length of the high bond point material limits, in this hypothetical example, the attainable machine direction elongation of the composite material because the high bond point material would act as a "stop" to prevent further or excessive stretching of the elastic substrate in the machine direction under the effect of stretching forces which are less than the failure strength of the high bond points, gathered material.

The high bond point nonwoven facing can also be a mechanically prestrained material. The term "mechanically prestrained" as used herein refers to a material that has undergone localized mechanical stretching to permanently elongate inelastic components of the material. By way of illustration, a composite of an inelastic nonwoven and an elastic substrate can be mechanically prestrained such that the composite is extensible beyond the original limits of the inelastic nonwoven. In particular embodiments, a disposable absorbent pant can incorporate a mechanically prestrained composite comprising a high bond point nonwoven facing bonded to an elastic substrate, which can either be untensioned or under tension in one or more directions.

While the mechanical fastening means of the present invention are shown and described herein in connection with children's toilet training pants, it is understood that such fastening means may be incorporated into various other disposable absorbent articles, such as diapers, adult incontinence garments, sanitary napkins and the like, as well as surgical bandages and sponges, without departing from the scope of the present invention.

Various materials and/or portions of materials used in the training pants 20 can optionally be formed of retractive materials, including but not limited to waist elastic members 54 and 56, side panels 34 and 134, outer cover, bodyside liner, absorbent assembly and fastening components. The retractive materials can be activated using heat, for example. Suitable devices incorporating activation mechanisms are disclosed in U.S. Pat. Nos. 4,640,726 issued Feb. 3, 1987 to Sallee et al. and 4,663,106 issued May 5, 1987 to Pomplun et al., which are incorporated herein by reference.

As various changes could be made in the above constructions and methods, without departing from the scope of the invention, it is intended that all matter contained in the above description and shown in the accompanying drawings shall be interpreted as illustrative and not in a limiting sense.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A mechanical fastening system for an article, said mechanical fastening system comprising:
   a stretchable loop fastener component mountable on the article and comprising an elastomeric substrate and a high bond point non-woven loop material secured to the elastomeric substrate, the bond points on the non-woven loop material being defined by discrete compression points, said non-woven loop material being substantially free from discrete compression points other than at said bond points; and
   a hook fastener component mountable on the article and adapted for releasable engagement with the loop fastener component;
   wherein the stretchable loop fastener component is stretchable relative to the hook fastener component when the fastener components are engaged.

2. The mechanical fastening system as set forth in claim 1 wherein a high bond point non-woven loop material has greater than 225 bond points per square inch.

3. The mechanical fastening system of claim 2 wherein the high bond point nonwoven loop material has at least 250 bond points per square inch.

4. The mechanical fastening system of claim 3 wherein the high bond point nonwoven loop material has at least 275 bond points per square inch.

5. The mechanical fastening system of claim 4 wherein the high bond point nonwoven loop material has at least 300 bond points per square inch.

6. The mechanical fastening system of claim 1 wherein the high bond point nonwoven loop material has a bond area of greater than 10 percent.

7. The mechanical fastening system of claim 6 wherein the high bond point nonwoven loop material has a bond area of greater than 20 percent.

8. The mechanical fastening system of claim 7 wherein the high bond point nonwoven loop material has a bond area of greater than 30 percent.

9. The mechanical fastening system of claim 1 wherein the high bond point nonwoven loop material is mechanically prestrained.

10. The mechanical fastening system of claim 9 wherein the high bond point nonwoven loop material is neck-stretched.

11. The mechanical fastening system of claim 1 wherein the stretchable loop fastener component can be elastically stretched at least 100 percent in at least one direction.

12. The mechanical fastening system of claim 1 in combination with a disposable absorbent article for personal wear, said disposable article comprising a body having first and second end regions and comprising an inner layer for contact with the wearer's skin, at least a portion of the inner layer being liquid permeable, an outer layer in opposed relation with the inner layer, and an absorbent layer disposed between the inner layer and the outer layer, the loop fastener component being disposed on the absorbent article in the first end region and the hook fastener component being disposed on the absorbent article in the second end region.

* * * * *